US005620434A

United States Patent [19]

Brony

[11] Patent Number: 5,620,434

[45] Date of Patent: Apr. 15, 1997

[54] MEDICINE VIAL LINK FOR NEEDLELESS SYRINGES

[76] Inventor: Seth K. Brony, 13064 Twelve Hills Rd., Clarksville, Md. 21209

[21] Appl. No.: 500,152

[22] Filed: Jul. 10, 1995

Related U.S. Application Data

[63] Continuation-in-part of Ser. No. 209,885, Mar. 14, 1994, Pat. No. 5,454,805.

[51] Int. Cl.$^6$ .......... A61B 19/00

[52] U.S. Cl. .......... 604/406; 604/403; 604/411; 604/415; 604/249; 604/905; 141/320; 141/357

[58] Field of Search .......... 604/905, 411, 604/283, 246, 249, 403, 406, 407, 408; 141/27, 26, 25, 322, 321, 320, 357, 346

[56] References Cited

U.S. PATENT DOCUMENTS

| | | | |
|---|---|---|---|
| 3,729,031 | 4/1973 | Baldwin | 141/27 |
| 3,853,157 | 12/1974 | Madaio | 141/27 |
| 4,303,071 | 12/1981 | Smith . | |
| 4,317,448 | 3/1982 | Smith . | |
| 4,511,359 | 4/1985 | Vaillancourt . | |
| 4,650,475 | 3/1987 | Smith et al. . | |
| 4,662,878 | 5/1987 | Lindmayer . | |
| 4,784,657 | 11/1988 | Shimp et al. . | |
| 4,927,423 | 5/1990 | Malmberg . | |
| 5,006,118 | 4/1991 | Yule | 141/27 |
| 5,215,538 | 6/1993 | Larkin | 604/249 |
| 5,242,423 | 9/1993 | Goodsir et al. | 604/905 |
| 5,269,771 | 12/1993 | Thomas et al. | 604/283 |
| 5,484,070 | 1/1996 | Graham | 604/905 |

*Primary Examiner*—John G. Weiss
*Assistant Examiner*—Bruce Snow
*Attorney, Agent, or Firm*—Terrance L. Siemens

[57] ABSTRACT

A link for use between a needleless syringe and a liquid medicine vial may be used equally well with both Luer lock and slip tip syringes. An adapter flange forms both an anchor for a conventional Luer lock and a receiving receptacle for a conventional slip tip syringe. The bottom end of the receiving receptacle is capped with a cylindrical sieve providing multiple fluid flow paths. The vial end of the link is formed with a pocket for collecting fluid when the vial is inverted. Two separate versions are provided, with one having a flip-top cap flush with the top of the medicine vial and the other having a twist-off top extending above the top of the vial. An outer jacket, surrounding the vial top is an optional variation on either version and provides for resealing of multiple dose vials. A valve automatically seals the vial to protect against loss of fluid and contamination of remaining fluid within the vial, in the event that the vial is overturned.

4 Claims, 4 Drawing Sheets

MEDICINE VIAL LINK FOR NEEDLELESS SYRINGES

CROSS REFERENCE TO RELATED APPLICATION

This is a Continuation-In-Part of Ser. No. 08/209,885, filed Mar. 14, 1994 now U.S. Pat. No. 5,454,805.

BACKGROUND OF THE INVENTION

1. Field of the Invention

The present invention relates to an adapter for connecting a medicine vial to a needleless injector. More specifically, it relaxes to an adapter having multiple flow paths for the medicine. The medical field is seen as the most obvious benefactor from this unique article of manufacture. More generally, the invention could be used in any task where it is desired to remove a liquid from a container in a sealed, non-contaminating manner. For example, chemical laboratories could effectively use the link of this invention to transfer chemicals from vials and flasks without exposure to the ambient atmosphere.

Thus it can be seen that the potential fields of use for this invention are myriad and the particular preferred embodiment described herein is in no way meant to limit the use of the invention to the particular field chosen for exposition of the details of the invention.

A comprehensive listing of all the possible fields to which this invention may be applied is limited only by the imagination and is therefore not provided herein. Some of the more obvious applications are mentioned herein in the interest of providing a full and complete disclosure of the unique properties of this previously unknown general purpose article of manufacture. It is to be understood from the outset that the scope of this invention is not limited to these fields or to the specific examples of potential uses presented hereinafter.

2. Description of the Prior Art

Devices for transferring medicaments from vials to flasks are old and well known in the art. In the past it has been known to cork medicine flasks with rubber stoppers and withdraw the enclosed medicine by piercing the stopper with the needle of a Conventional syringe. This method always carried with it the danger of transferring minute particles of rubber into the vial and syringe, and ultimately into the body of the patient. Recently, concern for transmission of deadly viruses, such as the AIDS virus, has lead to the development of several varieties of needleless syringes. Of course, a syringe lacking a needle is useless for withdrawing liquid medicine from a vial by the old fashioned method of submerging the needle point beneath the surface of the liquid.

In accordance with conventional terminology, the term "slip tip syringe" used herein may be taken to mean any type of syringe plunger device absent the needle, and the term "Luer lock syringe" used herein may be taken to mean any type of syringe plunger device having a Luer lock adaptor and not having a needle. The term "needleless syringe" will be used to generically refer to both.

One variety of needleless syringe in common use is the type of syringe which is adapted to fasten to a conventional "Luer lock" fastener used for administering medical solutions intravenously. This fastener allows the feed tube to be changed without removing the administering needle from the body of the patient. Syringes exist which are adapted to fasten to these Luer locks for the purpose of administering single dose injections of medicament through an existing intravenous line.

Another type of needleless syringe is in common use which is herein referred to as a "slip tip" syringe. This variety of syringe has been developed recently to prevent accidental pricking of health care professionals in handling the syringe. The deadly AIDS virus is known to be carried in bodily fluids such as blood. For this reason, once a needle has been exposed to the fluid of an infected patient, it becomes a deadly sword, capable of killing with a single prick. In the slip tip syringe, the needle is not present upon the syringe except at the actual point of administration after which it is removed by any one of several mechanical expedients presently available. The following known priori art has been directed to providing transfer of medicament from vial containers to syringes. As will be seen, the simplicity and effectiveness of my invention is not rivaled in the prior art.

U.S. Pat. No. 4,662,878, issued to Istvan Lindmayer on May 5, 1987, shows a medicine vial adaptor for a needleless injector. The patent shows a disposable plastic adaptor connecting a medicine vial to a needleless injector. In essence, the adapter contains its own needle which is used to withdraw the medicine after the syringe is connected to the adapter. By contrast, the instant invention does not use any needle and is thus truly "needleless."

U.S. Patent No. 4,650,475, issued to Carol Smith et al. on March 17, 1987, discloses a method and apparatus for the injection of pharmaceutical ingredients. The patent shows a penetrator (needle) for fully draining the liquid from a multi-dose vial when drawing liquid into a syringe. By contrast, the device of the instant invention does not use a penetrator or anything resembling a needle and therefore totally eliminates the risk of accidental sticking of the user.

U.S. Patent No. 4,317,448, issued to Philip E. Smith on March 2, 1982, shows a syringe-type liquid container dispenser adapter. The patent teaches the withdrawal of fluid from a vial with a needleless syringe. The conical insertion opening for receiving the nozzle of the syringe tends to constrict the flow of fluid during withdrawal. There is not provided a multiple flow path for the fluid. By contrast, the instant invention provides an open syringe nozzle insertion area and a multiple flow path for the fluid.

U.S. Pat. No. 4,303,071, issued to Philip E. Smith on Dec. 1, 1981, shows a syringe-type liquid container dispenser adapter. The patent is similar to Lindmayer and Smith et al. above in that a needle is provided as a part of the adapter structure. By contrast, the device of the instant invention requires no needle or sharp edges.

U.S. Pat. No. 4,511,359, issued to Vincent L. Vaillancourt on Apr. 16, 1985, shows a sterile connection device. As above, the patent requires a needle to penetrate a sealing membrane for fluid transfer. By contrast, the instant invention requires no needle for operation, it being a primary object of my invention to eliminate needles entirely.

U.S. Pat. No. 4,927,423, issued to Bengt Malmberg on May 22, 1990, shows a connector and a disposable assembly utilizing said connector. As in most of the above patents an internal piercing member is built into the connector for piercing a membrane covering the medicament. By contrast, the instant invention uses no needles or piercing members.

U.S. Pat. No. 4,784,657, issued to Lawrence A. Shimp et al. on Nov. 15, 1988, shows a syringe-vial material transfer interconnector. This patent is not directed to the transfer of fluids. By contrast, the instant invention is for the transfer of fluids from a vial to a syringe in a safe, sanitary, and needleless manner.

It will be noted that most of the prior art devices require some sort of needle or penetrating device to operate. Smith ('488) requires no needle but does not provide multiple flow paths. Shimp et al. requires no needle but is not suitable for withdrawing liquids.

None of the above inventions and patents, taken either singly or in combination, is seen to describe the instant invention as claimed.

SUMMARY OF THE INVENTION

Briefly, the invention comprises a link for use between a needleless syringe and a liquid medicine vial. The link may be used equally well with both Luer lock and slip tip syringes. An adapter flange forms both an anchor for a conventional Luer lock and a receiving receptacle for a conventional slip tip syringe. The bottom end of the receiving receptacle is capped with a cylindrical sieve providing multiple fluid flow paths. The vial end of the link is formed with a pocket for collecting fluid when the vial is inverted. Two separate versions are provided, with one having a flip-off top and the other having a twist-off top. The flip-off top version may be varied so as to attach to the vial neck for resealing multiple dose vials. An outer jacket surrounding the vial top is an option on either embodiment.

In an alternative embodiment, the link incorporates a valve for preventing Unintended discharge from the vial, should the vial become overturned. The valve is normally biased into the closed position by spring action, but is easily opened by inserting a syringe into the vial in order to extract fluid contained therein.

A spring action valve both protects against unintended discharge and possible contamination by air entering the vial, but further has the advantage that it acts automatically both in closing the vial and in yielding access thereto. No additional step dedicated to opening the valve, or separate operation, is required to cause the valve either to open or to close.

Accordingly, it is a principle object of the invention to provide a new and improved medicine vial adapter link for needleless syringes which overcomes the disadvantages of the prior art in a simple but effective manner.

It is a major object of this invention to provide such a link which does not contain or require any penetration by or use of a sharp object to establish fluid communication.

It is another major object of this invention to provide such a link which is suitable for use with either single dose or multiple dose vials with effective resealing of partially used contents.

It is another object of the invention to provide such a link which is suitable for use either with a slip tip syringe or with a Luer lock syringe without modification.

It is another object of the invention to provide such a link with a syringe nozzle receiving receptacle which in no way constricts cross-sectional area of the nozzle or in any other way restricts the flow of fluid.

It is another object of the invention to provide such a link with a syringe nozzle receiving receptacle which provides multiple fluid flow paths.

It is another object of the invention to provide such a link with a syringe nozzle receiving receptacle having a cylindrical sieve element which serves both as a filter and a multiple flow path element.

It is another object of the invention to provide such a link with a twist-off top extending above the upper opening in the vial, the top providing protective, contamination free sealing of partially used vial contents.

It is another object of the invention to provide such a link with a flip-off top substantially flush with the upper opening in the vial, the top providing protective, contamination free sealing of partially used vial contents.

It is another object of the invention to prevent unintended discharge of fluid contents from the vial.

It is another object of the invention to provide an automatically acting valve to prevent unintended discharge of fluid contents, which valve is opened by insertion of a syringe, and which is not dependent upon a dedicated step or manual operation to open and close.

Finally, it is a general goal of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

The present invention meets or exceeds all the above objects and goals. Upon further study of the specification and appended claims, further objects and advantages of this invention will become apparent to those skilled in the art.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
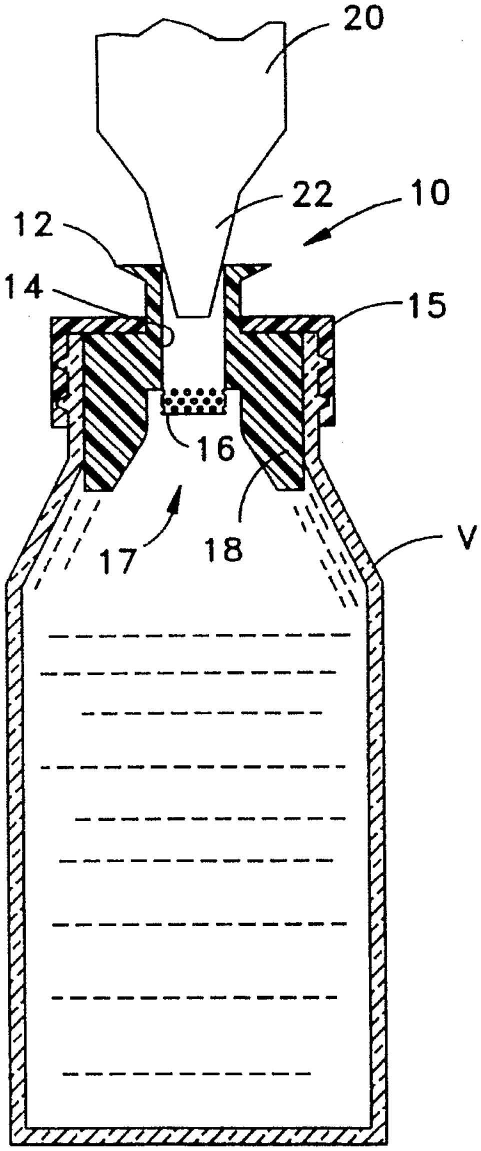
FIG. 1 is a cross-sectional view of a first embodiment of the invention shown attached to a medicine vial and showing a partially broken away slip tip syringe in position for use.
Figure 2:
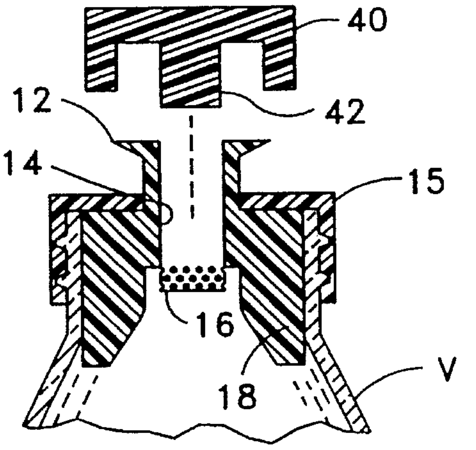
FIG. 2 is an exploded cross-sectional view of the first embodiment of the invention showing, somewhat schematically, a twist-off top protector.
Figure 3:
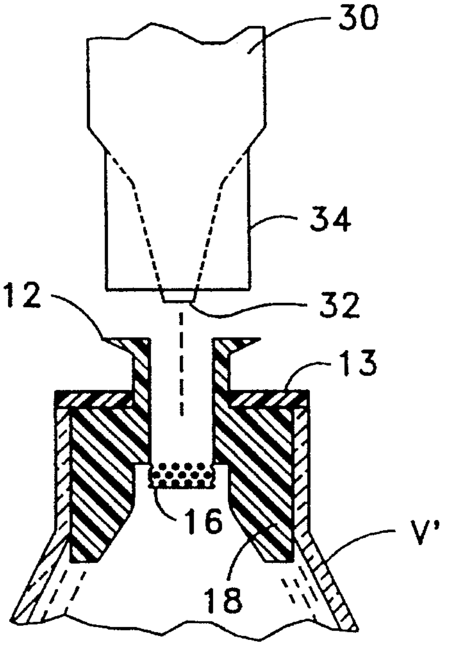
FIG. 3 is an exploded cross-sectional view of the first embodiment of the invention with the twist-off top removed, showing a partially broken away Luer lock syringe ready to be positioned for use.
Figure 4:
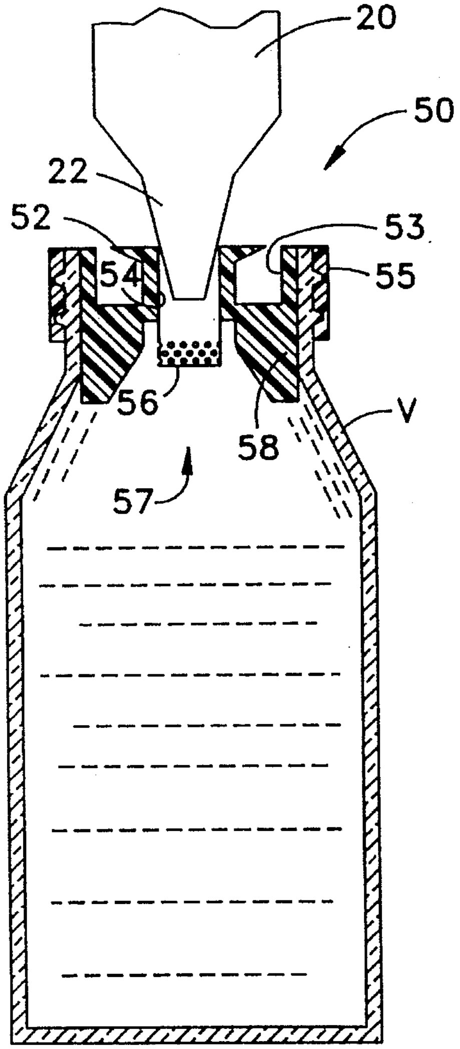
FIG. 4 is a cross-sectional view of a second embodiment of the invention shown attached to a medicine vial and showing a partially broken away slip tip syringe in position for use.
Figure 5:
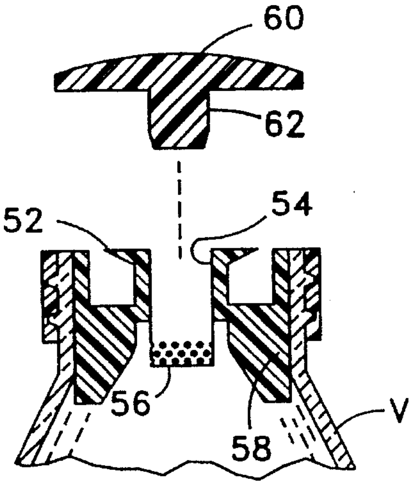
FIG. 5 is an exploded cross-sectional view of the second embodiment of the invention showing, somewhat schematically, a flip-off top protector.
Figure 6:
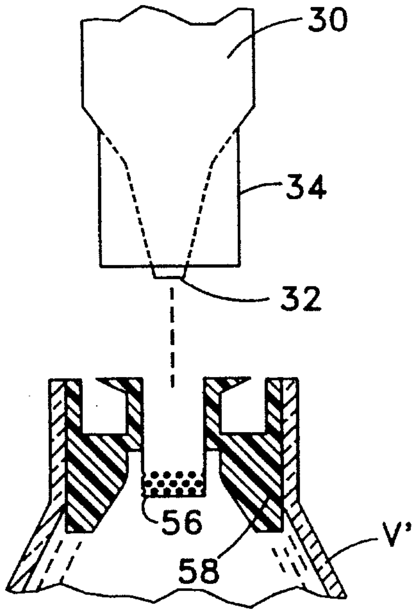
FIG. 6 is an exploded cross-sectional view of the second embodiment of the invention with the flip-off top removed, showing a partially broken away Luer lock syringe ready to be positioned for use.

The medicine vial link for needleless syringes of the first embodiment of the present invention is generally shown in FIGS. 1–3 and designated by arrow 10 of FIG. 1. The device comprises the following main portions: link parts 12–18, and twist-off top 40. The medicine vial link for needleless syringes of the second embodiment of the present invention is generally shown in FIGS. 4–6 and designated by arrow 50 of FIG. 4. The device comprises the following main portions: link parts 52–58, and flip-off top 60.

Turning first to FIGS. 1–3, the link 10 is shown attached to the top of medicine vial V. The slip tip syringe 20 of FIG. 1 and Luer lock syringe 30 of FIG. 3 are the conventional plunger type and only shown schematically. The artisan will be familiar with the details of the medical syringes. Jacket 15 is shown threaded to the upper portion of vial V. Main portion 18 of the link includes a central upstanding annular portion 11 which rises through a central aperture in jacket 15 to a point substantially higher than the upper opening in vial V. The upstanding annular portion has an inner bore 14 whose diameter is suitable to firmly surround a nozzle tip 22 of a slip tip syringe 20. The material is preferably flexible so as to expand as conical nozzle tip 22 is forced into the bore, thus forming a sealing fit. The upper rim of annular portion 12 is expanded radially outward to form a Luer lock anchor 12. Anchor 12 is used to secure and seal a Luer lock type syringe tip 32 in bore 14 as seen in FIG. 3. Thus, either a slip tip or Luer lock syringe can be sealed quickly to the top of a vial fitted with the link of this invention.

Turning to FIG. 12 there is shown a twist-off top 40 which has a depending plug 42 which fits in bore 14 as the top is lowered over the link body 18. This serves the function of expelling air from bore 14 as well as tightly sealing the vial for possible reuse. The convenient twist-off top of this embodiment is made accessible by the extension of the link above the top surface of the bottle. As will be seen in the ensuing discussion of the second embodiment (FIGS. 4–6), a flip-off top is also possible.

Lower portion 17 of link 18 is formed as a well for collecting a pool of fluid as the vial is inverted prior to withdrawing with the syringe plunger (not shown). A series of tiny holes 16 are arranged radially around a bottom diaphragm portion cowering the end of bore 14. These holes serve to provide multiple fluid flow paths as well as to afford a certain degree of filtration to the fluid. A minor variation on the jacket and vial is shown in FIG. 3 where vial V' has a smooth outer surface with no threads, and cap 15 of FIG. 1 has been replaced with a simple washer-like cap 13. The artisan will recognize that if a tight enough frictional fit is made between the link and the vial's inner surface there is no need for any cap.

A second embodiment of the invention will now be described with respect to FIGS. 1–3. The primary difference in this embodiment is that the top of the link is substantially flush with the top opening in the vial V. To this end, upstanding central annular portion of link 58 is recessed in annular depression 53. The top surface of the annular portion, containing Luer anchor 52, is substantially flush with the plane of the top opening in vial V.

As seen in FIGS. 4–6, the second embodiment of link 50 is shown attached to the top of medicine vial V. The slip tip syringe 20 of FIG. 4 and Luer lock syringe 30 of FIG. 6 are the conventional plunger type and only shown schematically. Jacket 55 is shown threaded to the outer upper portion of vial V. Main portion 58 of the link includes a central upstanding annular portion 54 which rises inside annular depression 53 in link 50 to a point substantially flush With the upper opening in vial V. The upstanding annular portion has an inner bore 54 whose diameter is suitable to surround firmly a nozzle tip 22 of a slip tip syringe 20. The material is preferably flexible so as to expand as conical nozzle tip 22 is forced into the bore, thus forming a sealing fit. The upper rim of the upstanding annular portion is expanded radially outward to form a Luer lock anchor 52. Anchor 52 is used to secure and seal a Luer lock type syringe tip 32 in bore 54 as seen in FIG. 6. Thus, either a slip tip or Luer lock syringe can be sealed quickly to the top of a vial fitted with the second embodiment of the link of this invention.

Turning to FIG. 5 there is shown a flip-off top 60 which has a depending plug 62 which fits in bore 54 as the top is lowered over the link body 58. This serves the function of expelling air from bore 54 as well as tightly sealing the vial for possible reuse. The flip-off top of this embodiment is made possible by the flush arrangement of the link with respect to the top surface of the bottle.

Lower portion 57 of link 58 is formed as a well for collecting a pool of=fluid as the vial is inverted prior to withdrawing with the syringe plunger (not shown). A series of tiny holes 56 are arranged radially around a bottom diaphragm-like portion covering the end of bore 54. These holes form a sieve and serve to provide multiple fluid flow paths as well as to afford a certain degree of filtration to the fluid. A minor variation on the jacket and vial is shown in FIG. 6 where vial V' has a smooth outer surface with no threads and jacket 55 of FIG. 3 has been eliminated.

In both embodiments, that of FIGS. 1–3 and that of FIGS. 4–6, a fluid retention valve arrangement is optionally incorporated to prevent unintended discharge of medicament or other contained fluid in the event that vial V is overturned.

Figure 7:
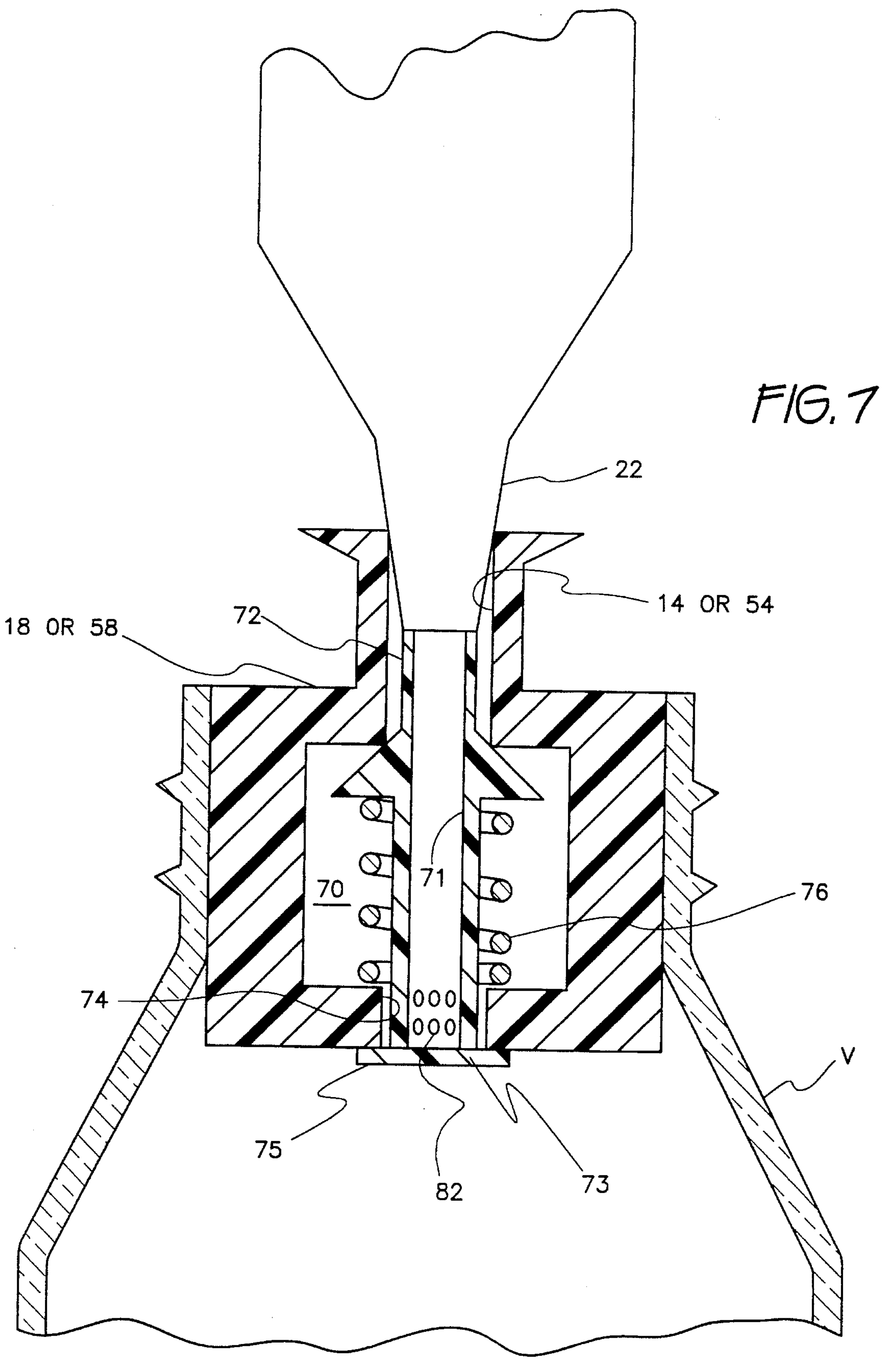
FIG. 7 is a cross-sectional detail view of an alternative embodiment of the invention, incorporating a spring operated valve for preventing unintended discharge of liquid from the vial.

Referring now to FIG. 7, there is a bore 14 formed in main portion 18 of the link, or a corresponding inner bore 54 formed in link body 58. In either bore 14 or 54, there is optionally provided a valve chamber 70 housing a valve 72. Valve 72 moves vertically downwardly, as depicted in FIG. 7, to uncover aperture 74 communicating between bore 14 or bore 54, and valve chamber 70. Valve 72 comprises a hollow body 71 having a plurality of holes 82 formed therein. Holes 82 extend only radially through body 71. A floor 73 closes the bottom of body 71. A flange 75 extends from body 71 beyond the diameter of passageway 74, thereby closing passageway 74 when flange 75 abuts main portion 18 of the link, or, alternatively, when flange 75 abuts link body 58.

Valve 72 is normally urged into the closed position depicted in this Figure by a spring 76. Spring 76 exerts a force easily overcome by insertion of nozzle tip 22 (see FIG. 1 or 4) into the link member 18 or 58. When nozzle tip 22 is not present, valve 72 closes passageway 74, and fluid stored in vial V is retained.

Figure 8:
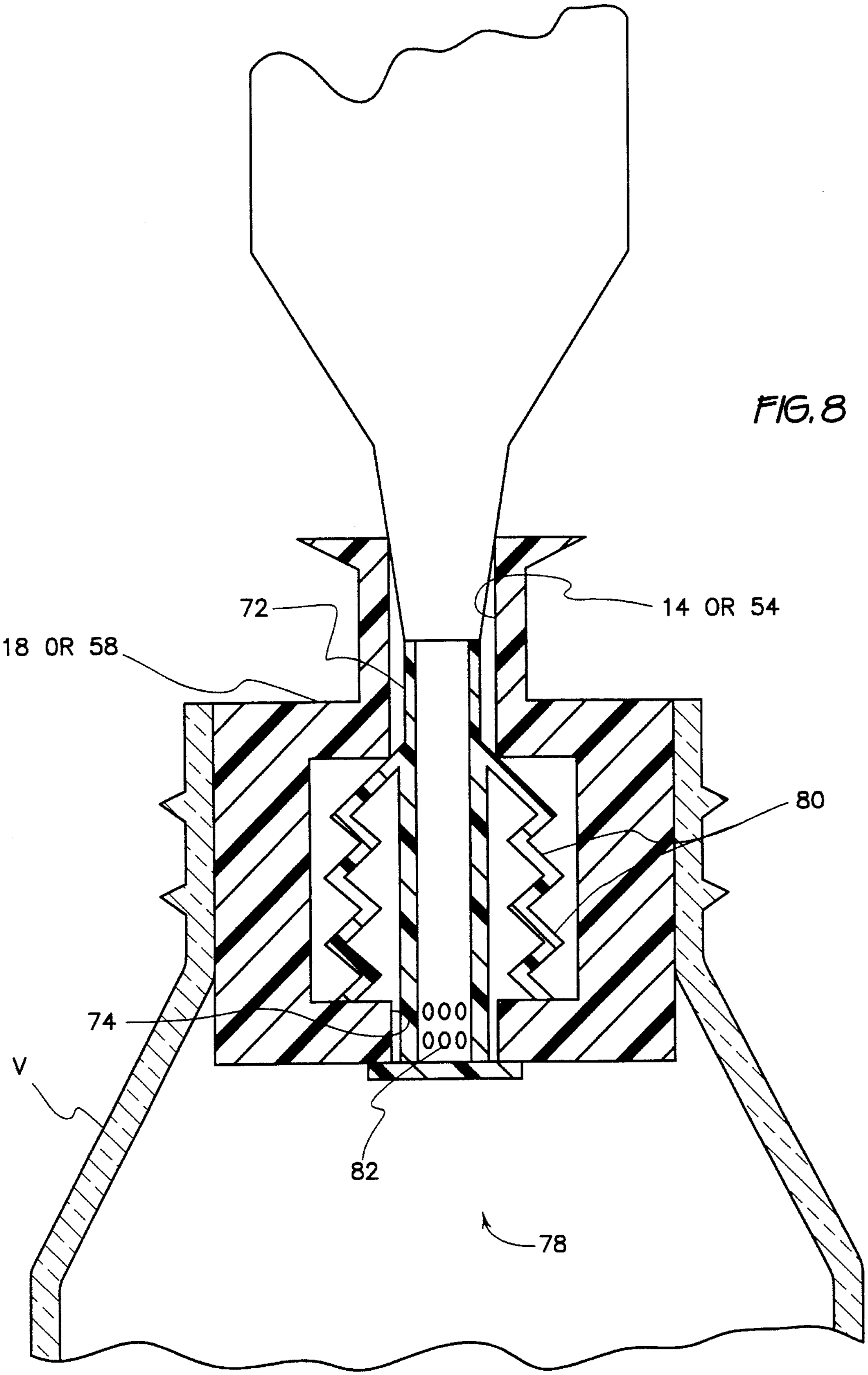
FIG. 8 is a cross-sectional detail view of an alternative embodiment of the invention, incorporating a resilient valve for preventing unintended discharge of liquid from the vial.

Biasing of valve 72 is not necessarily dependent upon spring 76 to close. As shown in FIG. 8, an alternative valve 78 may be formed from a resilient material so that the tendency to close is inherent within valve 78. In the depiction of FIG. 8, valve 78 comprises a bellows joint 80 which constantly attempts to expand of its own accord, thus causing valve 78 to seal aperture 74. As in the previous embodiment, resilience of bellows joint 80 is overcome by manually inserting nozzle tip 22 into link member 18 or 58.

Of course, it will be recognized that in appropriate embodiments, syringe tip 32 will be present rather than nozzle tip 22, valve 72 or 78 being employable with any of the embodiments of the main link member.

The operation of the invention will be briefly described now in order to highlight some of the novel aspects of this unique construction. A vial of medicine or drugs is first equipped with the link shown herein. Note that vials so equipped could be stored normally because the flip-off or twist-off tops will seal the vials in an airtight manner. When it is desired to fill a needleless syringe from one of the vials, the top is first removed and then the nozzle tip of the syringe is inserted into the resilient annular bore of the link. If the syringe is a Luer lock type, the Luer lock anchor is fastened at this time. The vial and syringe are then inverted causing liquid medicament to collect around the perforated end of cylinder blind bore 80. The syringe plunger is then withdrawn pulling the liquid into the syringe body. Note this withdrawal must be forcible because a vacuum is being created in the vial as the liquid is withdrawn and the air not replaced. It is intentionally done this way to prevent air bubbles from contaminating the fluid in the vial as it is being filled in the area of an infected patient. The liquid is drawn out through holes 82 78 on the vial end of the link. Holes 82 function similarly to holes 56 of the embodiment of FIGS. 1–6. These multiple fluid paths allow the medicine to be withdrawn much more easily than if a single tiny path, such as a needle, were present.

Valve arrangement of either FIG. 7 or FIG. 8 may be incorporated, and acts automatically to open and close access to the vial. No special attention need be paid by the user to effect valve operation.

It is to be understood that the provided illustrative examples are by no means exhaustive of the many possible uses for my invention.

From the foregoing description, one skilled in the art can easily ascertain the essential characteristics of this invention and, without departing from the spirit and scope thereof, can make various changes and modifications of the invention to adapt it to various usages and conditions. For example, the artisan could easily ascertain how to adapt various commercially available twist-off and flip-off tops to the link of this invention. Also sizing the various parts so as to fit different types of liquid containers and different types of withdrawal devices is well within the realm of the artisan.

It is to be understood that the present invention is not limited to the sole embodiment described above, but encompasses any and all embodiments within the scope of the following claims:

I claim:

1. An adapter link for providing sealed fluid medicament communication between a medicine vial having an opening for access and a needleless medication dispensing syringe having a conical nozzle tip, said adapter link comprising:

a resilient, tubular, generally cylindrical body member having a smooth outer surface for tightly fitting the inside of the opening formed in the medicine vial, and an outer periphery;

an upstanding annular portion formed in said body portion, having an upper rim around said outer periphery;

means defining a smooth central aperture formed in said upstanding annular portion, for sealably receiving said conical nozzle tip of said syringe, said aperture formed as a blind bore extending partially through said body member; and a valve disposed within said body member, having automatically operating means for maintaining said blind bore closed, and for opening said valve responsive to insertion of the conical nozzle tip of the syringe into said aperture formed in said body member, wherein said upper rim on said upstanding annular portion of said body is expanded radially when the conical nozzle tip of the syringe is received in said blind bore, said valve comprising a hollow valve body having a plurality of holes extending only radially through said hollow valve body and a floor closing the bottom of said hollow valve body, whereby said valve serves as a sieve for filtering fluid.

2. The adapter link of claim 1, said valve including a spring for maintaining said valve closed.

3. The adapter link of claim 1, further comprising flip-off top means for sealing said blind bore and substantially displacing air from most of said blind bore when said flip-off top means is inserted in said blind bore, wherein said flip-off top means lies substantially flush with the access opening formed in the medicine vial.

4. The adapter link of claim 1, further comprising twist-off top means for sealing said blind bore and substantially displacing air from most of said blind bore when said twist-off top means is inserted in said blind bore, wherein said twist-off top means lies substantially above the access opening formed in the medicine vial.

* * * * *